(12) United States Patent
Cermak et al.

(10) Patent No.: US 11,957,511 B2
(45) Date of Patent: Apr. 16, 2024

(54) COVERS FOR ULTRASOUND PROBE

(71) Applicant: CIVCO Medical Instruments Co., Inc., Kalona, IA (US)

(72) Inventors: Craig Joseph Cermak, Riverside, IA (US); Justin Paul Reynolds, Tiffin, IA (US); Geoffrey Scott Wagner, Fairfax, IA (US); Hannah Marie Pankow, Coralville, IA (US); Alexas Marin Swartz, Coralville, IA (US)

(73) Assignee: CIVCO MEDICAL INSTRUMENTS CO., INC., Kalona, IA (US)

( * ) Notice: Subject to any disclaimer, the term of this patent is extended or adjusted under 35 U.S.C. 154(b) by 1019 days.

(21) Appl. No.: 16/366,550

(22) Filed: Mar. 27, 2019

(65) Prior Publication Data

US 2019/0328357 A1 Oct. 31, 2019

Related U.S. Application Data

(60) Provisional application No. 62/648,426, filed on Mar. 27, 2018.

(51) Int. Cl.
| | | |
|---|---|---|
| *A61B 8/00* | (2006.01) | |
| *A61B 8/08* | (2006.01) | |
| *C09J 7/29* | (2018.01) | |
| *C09J 7/30* | (2018.01) | |
| *C09J 7/40* | (2018.01) | |

(Continued)

(52) U.S. Cl.
CPC .......... *A61B 8/4281* (2013.01); *A61B 8/0825* (2013.01); *A61B 8/403* (2013.01); *A61B 8/4422* (2013.01); *A61B 8/4444* (2013.01);

*C09J 7/29* (2018.01); *C09J 7/30* (2018.01); *C09J 7/40* (2018.01); *C09J 133/00* (2013.01);
(Continued)

(58) Field of Classification Search
CPC .............................. A61B 8/4281; A61B 8/403
See application file for complete search history.

(56) References Cited

U.S. PATENT DOCUMENTS

| | | |
|---|---|---|
| 4,002,221 A | 1/1977 | Buchalter |
| 4,059,098 A | 11/1977 | Murdock |

(Continued)

FOREIGN PATENT DOCUMENTS

| | | |
|---|---|---|
| CN | 102599937 A | 7/2012 |
| CN | 202636974 U | 1/2013 |

(Continued)

OTHER PUBLICATIONS

Ruhl et al. Characterization and modeling of poly (methyl methacrylate) and thermoplastic polyurethane for the application in laminated setups. Mechanics of Materials, vol. 113, 2017, pp. 102-111. https://doi.org/10.1016/j.mechmat.2017.07.018. (Year: 2017).*

(Continued)

*Primary Examiner* — Angela M Hoffa
*Assistant Examiner* — Younhee Choi
(74) *Attorney, Agent, or Firm* — Snyder, Clark, Lesch & Chung, LLP

(57) ABSTRACT

A cover for an ultrasound scanning assembly is provided, wherein the cover exerts compressive force on the patient during use. The cover includes an outer frame and a non-porous or porous film extending across the outer frame. The outer frame is formed of a soft touch material.

10 Claims, 5 Drawing Sheets

(51) Int. Cl.
*C09J 133/00* (2006.01)
*C09J 183/00* (2006.01)

(52) U.S. Cl.
CPC ........... *C09J 183/00* (2013.01); *A61B 8/4218* (2013.01); *C09J 2301/162* (2020.08)

(56) References Cited

U.S. PATENT DOCUMENTS

| | | | |
|---|---|---|---|
| 5,039,774 | A | 8/1991 | Shikinami et al. |
| 5,394,877 | A | 3/1995 | Orr et al. |
| 5,522,878 | A | 6/1996 | Montecalvo et al. |
| 5,727,550 | A | 3/1998 | Montecalvo |
| 5,770,801 | A | 6/1998 | Wang et al. |
| 5,782,767 | A | 7/1998 | Pretlow, III |
| 6,027,457 | A * | 2/2000 | Shmulewitz ........... A61B 90/17 600/562 |
| 6,039,694 | A | 3/2000 | Larson et al. |
| 6,106,473 | A * | 8/2000 | Violante ............. A61K 49/222 600/458 |
| 6,343,512 | B1 | 2/2002 | Bourne et al. |
| 6,719,699 | B2 | 4/2004 | Smith |
| 6,846,291 | B2 | 1/2005 | Smith et al. |
| 7,070,565 | B2 | 7/2006 | Vaezy et al. |
| 7,731,662 | B2 * | 6/2010 | Anderson ............... A61B 8/483 600/443 |
| 8,231,533 | B2 | 7/2012 | Buchalter |
| 2006/0241423 | A1 | 10/2006 | Anderson et al. |
| 2006/0264751 | A1 | 11/2006 | Wendelken et al. |
| 2007/0016053 | A1 * | 1/2007 | Lo ....................... A61B 5/02438 600/459 |
| 2008/0139944 | A1 | 6/2008 | Weymer et al. |
| 2008/0194959 | A1 | 8/2008 | Wang et al. |
| 2008/0269613 | A1 * | 10/2008 | Summers ............... A61B 8/483 600/459 |
| 2012/0302887 | A1 | 11/2012 | Anderson et al. |
| 2014/0180116 | A1 | 6/2014 | Lindekugel et al. |
| 2015/0141820 | A1 | 5/2015 | Yamada et al. |
| 2015/0245822 | A1 | 9/2015 | Kim et al. |
| 2015/0305709 | A1 | 10/2015 | Tomassi et al. |
| 2015/0351721 | A1 | 12/2015 | Vriezema et al. |
| 2016/0022244 | A1 * | 1/2016 | Courtney ............. A61B 8/4416 600/407 |
| 2017/0079846 | A1 * | 3/2017 | Locke ....................... B32B 5/02 |
| 2017/0128042 | A1 * | 5/2017 | Desai ................... A61B 8/4455 |
| 2020/0289087 | A1 * | 9/2020 | Beckers ............... A61B 8/4236 |

FOREIGN PATENT DOCUMENTS

| | | |
|---|---|---|
| CN | 105496458 A | 4/2016 |
| WO | 2006069579 A2 | 7/2006 |
| WO | 20150164708 A1 | 10/2015 |

OTHER PUBLICATIONS

International Search Report and Written Opinion issued in corresponding International Application No. PCT/US2019/024352 dated May 24, 2019, 12 pages.
"PS-2056 (Dev) Technical Datasheet," Plymer Science, Inc. May 1, 2015.
Invenia™ ABUS 2.0 Automated Breast Ultrasound. General Electric Company—Dec. 2018. Accessed online Mar. 27, 2019, 8 pages. https://www.gehealthcare.com/-/media/3ff8b17067c046949783bd8b7d3428b9.pdf.
"Sterile Gel-Free Transducer Cover with Adhesive," Safersonic, Nov. 2011, retrieved from: <https://www.safersonic.com/wp-content/uploads/2016/09/English-Sales-Flyer.pdf>.
"Adhesion Probe Covers," Ecolab, 2019, retrieved from: <https://www.ecolab.com/offerings/adhesion-probe-covers>.
"Why we have the only FDA-Cleared Viral Barrier," Sheathing Technologies, 2019, retrieved from: <http://www.sheathes.com/>.
ABUS Single-Use Stabilization Curved Membrane for the Invenia™ ABUS and somo•v™ ABUS Platinum. General Electric Company—2018. Accessed online Mar. 27, 2019, 1 page. https://services.gehealthcare.com/gehcstorefront/p/E8340AB.
ABUS Single-Use Stabilization Flat Membrane for the somo•v™ ABUS Insight. General Electric Company—2018. Accessed online Mar. 27, 2019, 1 page. https://services.gehealthcare.com/gehcstorefront/p/E8340AC.

* cited by examiner

COVERS FOR ULTRASOUND PROBE

CROSS-REFERENCE TO RELATED APPLICATION

The present application claims priority to U.S. Provisional Patent Application No. 62/648,426, filed Mar. 27, 2018, the entirety of which is hereby incorporated by reference herein.

BACKGROUND

This invention relates to medical devices and more particularly to ultrasound probes and devices for covering the probe.

Volumetric ultrasound scanning usually involves the movement of an ultrasound transducer relative to a tissue sample and the processing of ultrasound echoes to form an image representing at least one acoustic property of the tissue sample. Volumetric ultrasound scanning of the breast has been proposed as a complementary modality for breast cancer screening. More particular, known volumetric ultrasound scanning systems typically include a transducer unit that compresses the breast using a partially conformable, substantially taut membrane or film sheet, such as a fine polyester mesh membrane. An acoustic gel is applied to the side of the sheet in contact with the breast to assist in acoustically coupling the tissue to the ultrasound assembly. A transducer translation mechanism maintains the ultrasound transducer in contact with the other side of the membrane or film sheet while translating or sliding the ultrasound transducer thereacross to scan the breast.

Unfortunately, known membranes or films for use in such systems suffer from usability and hygiene concerns.

DETAILED DESCRIPTION OF THE PREFERRED EMBODIMENTS

The following detailed description refers to the accompanying drawings. The same reference numbers in different drawings may identify the same or similar elements. Also, the following detailed description does not limit the invention.

Implementations described herein relate to covers for ultrasound systems, in which the cover is urged into compressive relationship with a patient during use. Consistent with one implementation described herein, an ultrasound transducer cover may include an outer frame formed of a "soft touch" material, and a nonporous or porous film that extends across the outer frame. In another embodiment, the cover may be configured to receive an advanceable roll of film material, such that subsequent uses of the ultrasound system may be performed upon advancement of the roll of film material. In still another embodiment, the cover may include grooved "stand-offs" that project downwardly relative to a remainder of the cover. The grooves in the stand-offs may be sized to receive disposable portions of film material.

Figure 1:
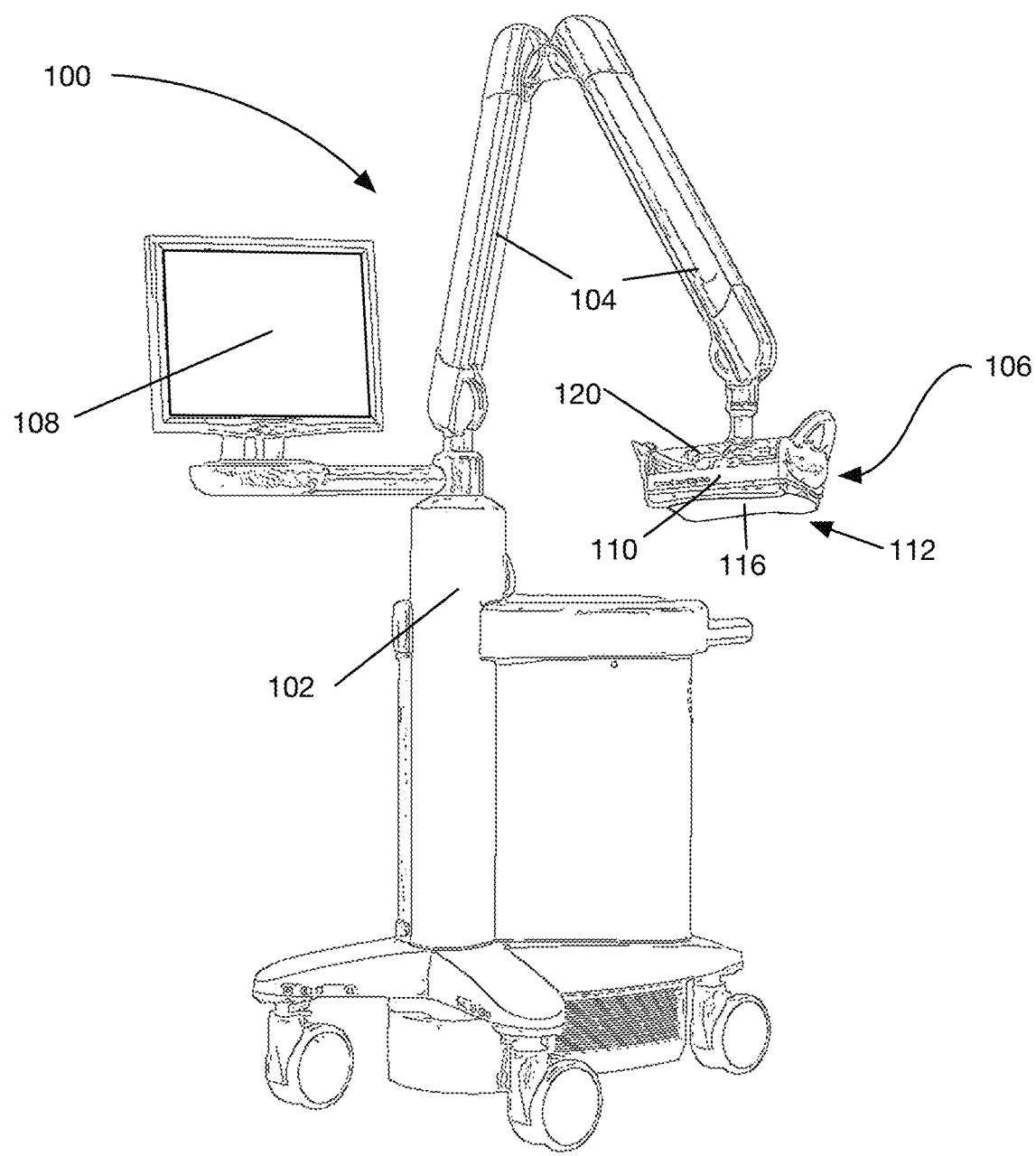
FIG. 1 is a perspective view of an ultrasound apparatus system for use with embodiments described herein.
Figure 2:
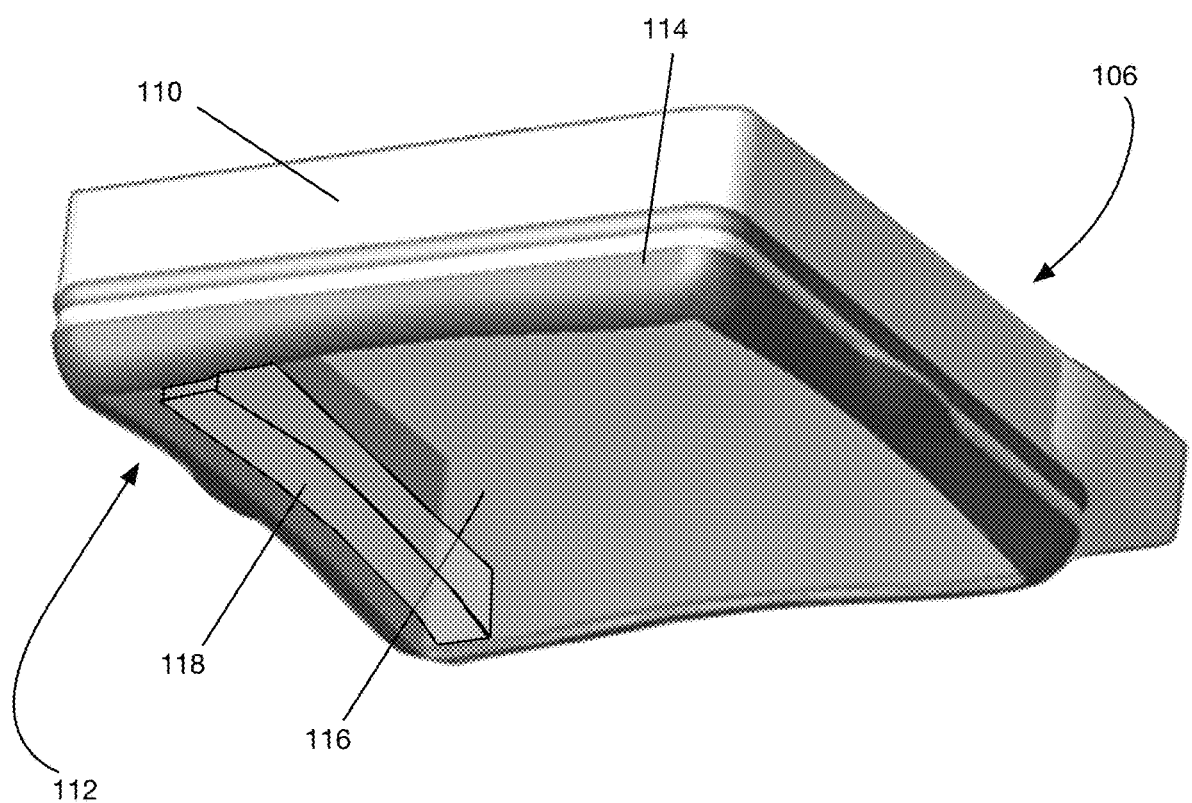
FIG. 2 is a bottom perspective view of a cover for the ultrasound system of FIG. 1.

FIG. 1 is a perspective view of a breast ultrasound scanning apparatus 100 consistent with embodiments described herein. As shown, breast ultrasound scanning apparatus 100 includes a frame 102, movable support arms 104, a compression/scanning assembly 106, and a display 108. FIG. 2 is a perspective view of a bottom of portion of compression/scanning assembly 106.

Consistent with embodiments described herein, one or more of frame 102 and compression/scanning assembly 106 may contain components necessary to generate appropriate ultrasound signals, for transmission via compression/scanning assembly 106. Movable support arms 104 may be mounted on or otherwise coupled to frame 102 to allow support arms to be moved relative to frame 102 in multiple degrees of freedom. For example, one or more hinges or joints may be used to couple support arms 104 to each other and to frame 102.

As shown in FIGS. 1 and 2, compression/scanning assembly 106 includes a generally rectangular housing 110 having a central aperture that extends therethrough. A cover 112 is provided in a patient-side of housing 110. Cover 112 acts as a physical interface between the patient and compression/scanning assembly 106. During use, compression/scanning assembly 106 is lowered toward a patient, such that cover 112 contacts and compresses the breast, usually toward the rib cage. Cover 112 may be a modular component configured to be periodically removed from compression/scanning assembly 106 and cleaned or replaced. For example, cover 112, may be clipped or otherwise secured to housing 110.

Consistent with embodiments described herein, cover 112 comprises an outer frame 114 and a film portion 116. In some embodiments, outer frame 114 is formed or is at least partially formed of a soft touch plastic or polymer material. Such a material substantially increases patient comfort during the scanning process, since, as mentioned above, compression/scanning assembly 106 is applies a compressive force to a patient during the procedure. In other embodiments, more rigid, non-soft touch materials may be used. Film portion 116 includes a film layer that is secured to outer frame 114. For example, film portion 116 may be heat sealed to outer frame 114. In other embodiments, alternative fastening mechanisms may be used, such as adhesives, or other bonding agents, or mechanical fastening devices, such as clips or grooves.

In some implementations, such as that shown in FIG. 2, film portion 116 includes a transparent or translucent material, to assist in positioning compression/scanning assembly 106 relative to the patient. Furthermore, consistent with embodiments described herein, film portion may be formed of either a non-porous material, or a porous material, such as a mesh layer. In a non-porous embodiment, an acoustic gel or lotion is applied to one or both sides of film portion 116 prior to use. As described in additional detail below, consistent with embodiments described herein, one or more hydrophilic layers may be applied to minimize or remove the need for acoustic gels or lotions. In a porous or mesh film embodiment, an acoustic gel or lotion may be applied to only one side and may be permitted to flow through the porous material. Cover 112 may then be cleaned after the procedure and prepared for reuse or replaced depending on the embodiment.

Compression/scanning assembly 106 includes an ultrasound transducer 118 mounted within housing 110. During use, ultrasound transducer 118 is swept across the top of the cover 112 in a generally arcuate trajectory to ultrasonically scan, for example, a compressed breast therethrough. In some embodiments, a top surface 120 of the compression/scanning assembly 106 is preferably translucent to visible light to allow the user to see therethrough and onto the top of the film portion 116, for facilitating ease of positioning. For embodiments in which the film portion 116 is also translucent to visible light, the skin of the compressed breast can itself be seen through the top surface 120.

Figure 3:
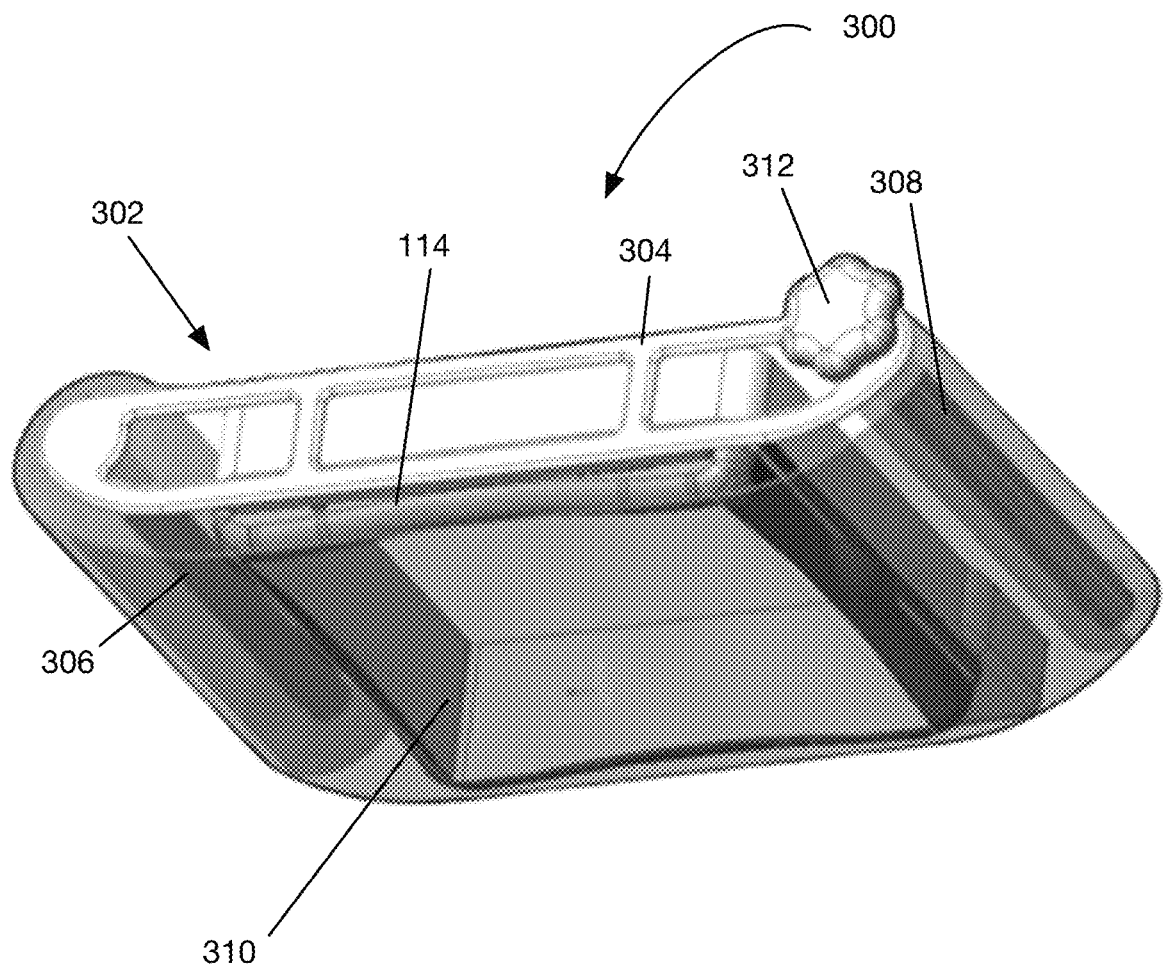
FIG. 3 is a bottom perspective view of an alternative cover for the ultrasound system of FIG. 1.

FIG. 3 is an isometric view of cover 300 depicting an alternative embodiment of cover 112 described above consistent with embodiments described herein. As shown in FIG. 3, cover 300 includes frame 114 and an advanceable film roll assembly 302. Advanceable film roll assembly 302 includes a rigid frame 304 and a pair of opposing rollers 306/308 positioned on opposite ends of rigid frame 304. Rigid frame 304 is secured to an outer periphery of compression/scanning assembly 106. As shown in FIG. 3, a bottom edge of rigid frame 304 is positioned upwardly relative to a bottom surface of cover frame 114, such that the rigid frame 304 does not contact the patient during use.

Rollers 306/308 are configured to receive opposite ends of a roll of film material 310. As shown in FIG. 3, a new roll of film material 310 may be placed onto roller 306 and its free end stretched across cover frame 114, such that a portion of film material 310 completely extends over frame 114. The free end is then secured to roller 308 (e.g., via an axial slot (not shown) formed in roller 308). An end of roller 308 may be provided with a roll advancement mechanism 312 (e.g., knob 312) that allows a user to advance the roll of material 310 for use with a new patient. In this manner, cover 300 may be used with multiple patients without requiring the device to be cleaned or cover 300 to be disposed of or replaced.

Figure 4:
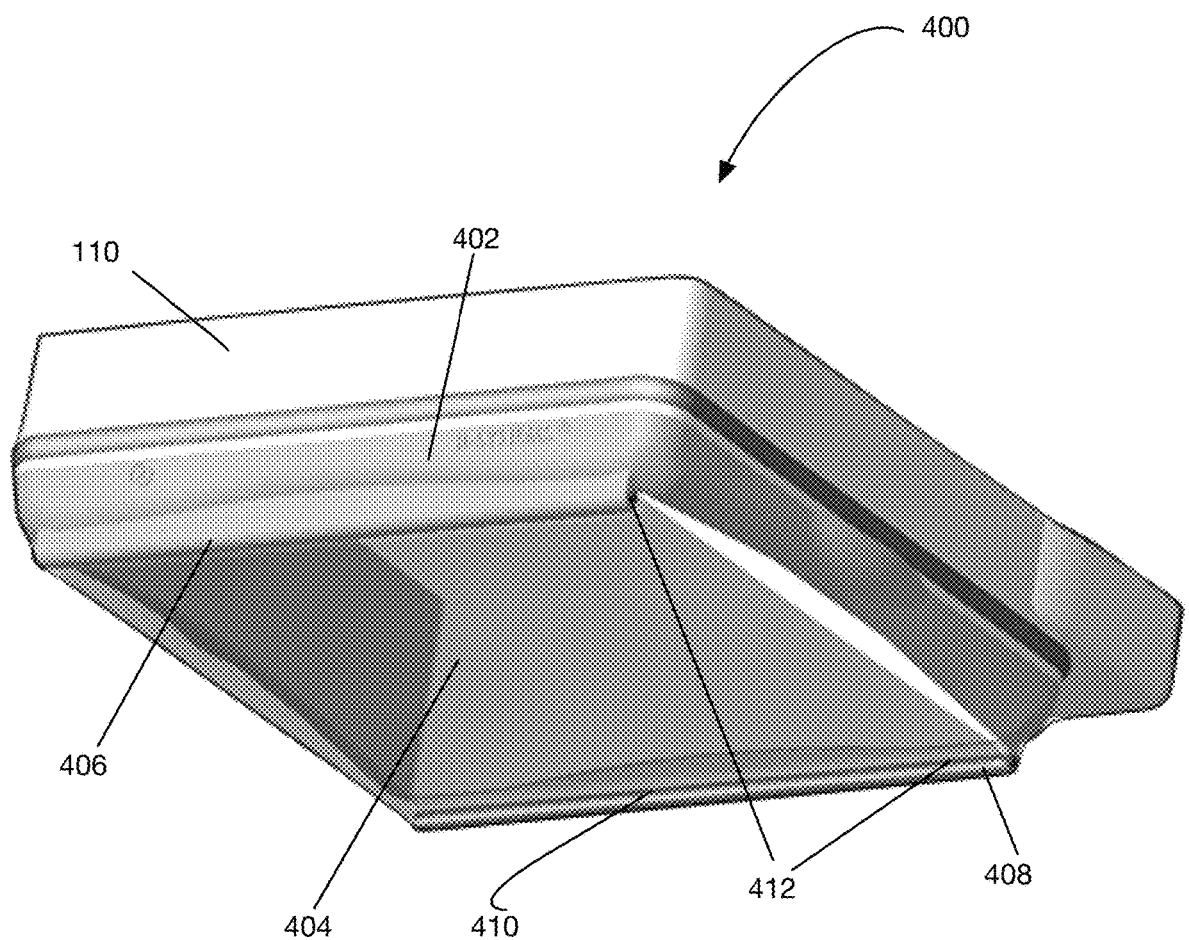
FIG. 4 is a bottom perspective view of yet another alternative cover for the ultrasound system of FIG. 1.

FIG. 4 is an isometric view of cover 400 depicting another alternative embodiment of cover 112 described above. As shown, cover 400 includes outer frame 402 and film portion 404. Similar to frame 114 described above, frame 402 may be formed of a soft-touch material that is comfortable during compression of a patient body part (e.g., a breast), as described herein. In addition, frame 402 includes a pair of opposing stand-offs 406 and 408, which project downwardly from opposite sides of frame 402. Stand-offs 406/408 each include an inwardly facing groove 410 sized to receive opposing edges 412 of film portion 404.

In one implementation, opposing edges 412 may be formed into semi-rigid or rigid cylindrical portions sized to frictionally fit within grooves 410. In other embodiments, opposing edges 412 of film portion 404 may be secured (e.g., adhered) to rods or dowels, formed of a rigid or semi-rigid material (e.g., plastic or metal), which collectively are sized to be received within grooves 410. Such a configuration allows for rapid removal and replacement of film portion 404, while reusing outer frame 402.

Consistent with embodiments described herein, in lieu of acoustic gel or lotion being applied directly to an inner surface of film material (e.g., film portion 116, film material 310, and film portion 404), a water tray or bladder bag may be provided within the cover (e.g., cover 112, 300, or 400) and that directly contacts the inner surface of the film material. Transducer 118 may be positioned within the water tray or bladder bag, which provides sufficient acoustic coupling between the transducer and the film material.

Figure 5A:
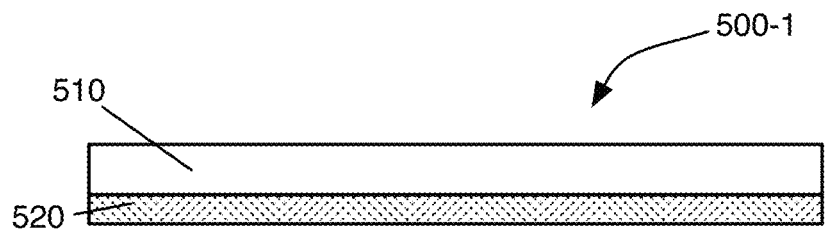
FIGS. 5A-5D illustrate cross-sectional views of exemplary implementations of the film portion of FIGS. 1-4.

FIGS. 5A to 5D illustrate cross-sectional views of exemplary implementations of film portion 116/310/404 (referred to generally as film portions 500-1 to 500-4, respectively). As shown in FIG. 5A, film portion 500-1 includes a substrate layer 510 and a hydrophilic coating layer 520. In one embodiment substrate layer 510 comprises a polyurethane carrier or material having a thickness ranging from approximately 0.025 to 1.0 millimeters (mm) and a hydrophilic coating layer 520 applied on a side of substrate layer 510 that is positioned to contact the patient. As described above, substrate layer 510 may include a nonporous (e.g., solid) or porous (e.g., mesh or screen) material.

In one embodiment, hydrophilic coating layer 520 may include an ultra-violet (UV) light or heat curable materials, such as polyvinylpyrrolidone/polyurethane (PVP/PU) or poly methacrylate (PM), having a thickness in the range of approximately 2 to 5 microns. During manufacture, hydrophilic coating layer 520 may be applied to substrate layer 520 and cured via exposure to UV light or exposing the layer to heat.

During use, hydrophilic coating layer 520 may be activated using only water or saline to provide the requisite acoustic coupling interface between a substrate layer 510 and a patient. By utilizing a hydrophilic coating layer 520, acoustic coupling may be provided without the messy cleanup required by conventional acoustic coupling gels or lotions. In some implementations, an acoustic coupling gel may be applied to an inside of substrate layer 510 prior to applying film portions 500 to frame 114/402 to acoustically interface with ultrasound transducer 118.

Figure 5B:
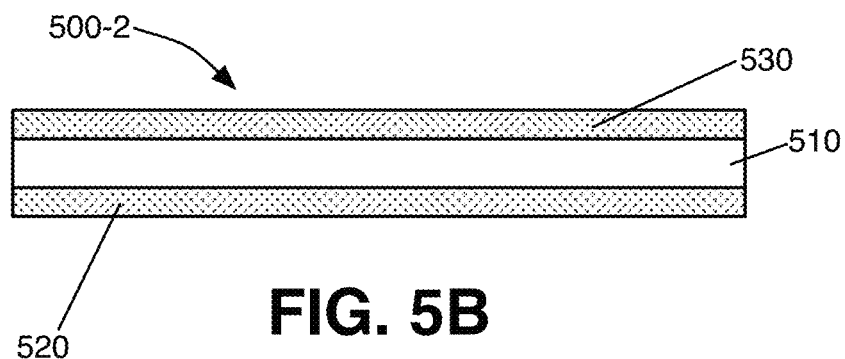

FIG. 5B illustrates an embodiment of film portion 500-2. As shown, in addition to substrate layer 510 and first hydrophilic coating layer 520, film portion 500-2 may further include a second hydrophilic coating layer 530 applied to substrate layer 510 opposite to first hydrophilic coating layer 520. In this configuration, hydrophilic coating layers 520/530 may be activated using only water or saline to provide the requisite acoustic coupling interface between transducer 118, substrate layer 510, and the patient.

Figure 5C:
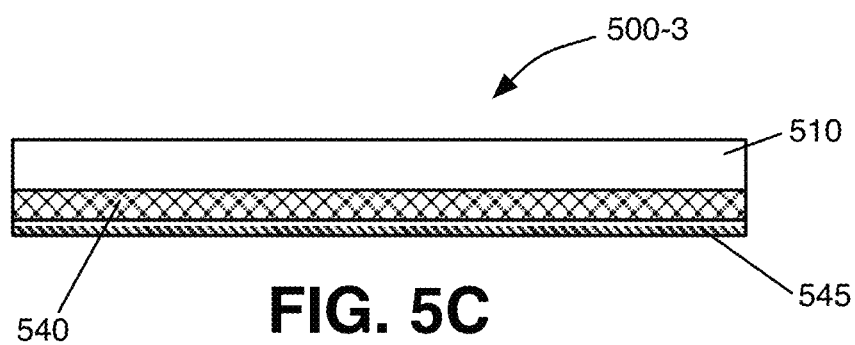

In another implementation, as shown in FIG. 5C, film portion 500-3 includes substrate layer 510, an adhesive layer 540, and a removable release layer 545. As with film portions 500-1 and 500-2 described above, substrate layer 510 may include a polyurethane film carrier or material, such as polyether polyurethane having a thickness ranging from approximately 0.025 to 1.00 millimeters (mm). Adhesive layer 540 may include a silicone-based adhesive, having, for example, an adhesion (or removal force) of between 0.2 and 0.8 Newtons (N) per 25 millimeters (mm). The relatively low removal force of such a silicon-based adhesive renders film portion 500-3 generally repositionable after initial deployment.

In other embodiments, adhesive layer 540 may include an acrylic or synthetic rubber-based adhesive material. Such non-silicone-based adhesives may exhibit significantly higher removal forces (e.g., as high as 16.7N per 25 mm). An adhesive having a higher removal force may be desirable in some circumstances, such as where slippage of the film portion during use is a concern.

Consistent with embodiments described herein, adhesive layer 540 may be applied (e.g., coated) onto substrate layer 510 at a coat weight ranging from approximately 100 to 200 grams per square meter (gsm), and preferably at a coat weight of 150 gsm, resulting in adhesive layer 540 having an applied thickness ranging from 0.025 to 0.2 mm (e.g., 0.15 mm).

During manufacture and prior to use, film portion 500-3 includes release layer 545 (also referred to as a liner or release liner) that is provided on adhesive layer 540 to protect the tackiness of adhesive layer 540 and to prevent adhesive layer 540 from adhering to other items or itself prior to use. In one implementation, release layer 545 comprises a polycarbonate layer. Consistent with embodiments described herein, release layer 545 is removed (e.g., peeled off) prior to using film portion 500-3, e.g., prior to adhering film portion 500-3 to a patient. In some embodiments, release layer 545 may include an edge area or slit that allows release layer 545 to be easily removed from adhesive layer 540 when film portion 500-3 is ready for use.

Figure 5D:
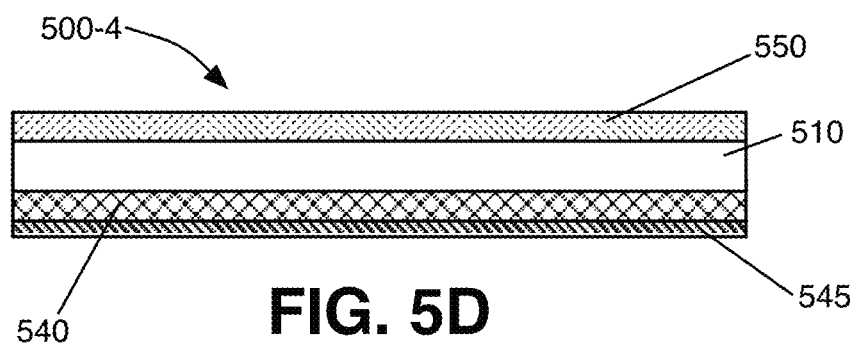

In still another implementation, as shown in FIG. 5D, film portion 500-4 includes substrate layer 510, hydrophilic layer 550, adhesive layer 540, and removable release layer 545. As with film portion 500-3 and 500-2 described above, adhesive layer 540 may be applied to a patient side of film portion 500-4. Consistent with the embodiment of FIG. 5D, a hydrophilic layer 550 is applied to an opposite side of substrate layer 510 from adhesive layer 540.

In this configuration, hydrophilic coating layer 550 may be activated using only water or saline to provide the requisite acoustic coupling interface between transducer 118 and substrate layer 510. During use, release layer 545 is removed and film portion 500-4 is positioned and adhered to the patient at a desired location.

The foregoing description of exemplary implementations provides illustration and description but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A cover for an ultrasound scanning assembly, wherein the cover exerts compressive force on a patient during use, the cover comprising:
   an outer frame; and
   a film material extending across the outer frame,
   wherein the film material comprises:
      a substrate layer having a first surface and a second surface;
      a first hydrophilic layer provided on the first surface of the substrate layer; and
      a second hydrophilic layer provided on the second surface of the substrate layer;
   wherein the film material further comprises a sheet having two opposing outer edges formed into semi-rigid or rigid cylindrical portions,
   wherein the outer frame comprises a pair of stand-offs projecting downwardly on opposite sides of the outer frame,
   wherein each stand-off of the pair of stand-offs comprises an inwardly directed groove, and
   wherein the inwardly directed grooves are configured to receive the semi-rigid or rigid cylindrical portions of the outer edges of the sheet of the film material therein.

2. The cover of claim 1, wherein the substrate layer comprises a polyurethane film material.

3. The cover of claim 2, wherein the polyurethane film material has a thickness ranging from approximately 0.025 to 1.00 millimeters.

4. The cover of claim 1, wherein each of the first hydrophilic layer and the second hydrophilic layer comprises one of an ultra-violet (UV) light curable hydrophilic material or a heat curable hydrophilic material.

5. The cover of claim 1, wherein the outer frame is formed of a soft touch material.

6. The cover of claim 1, wherein the film material comprises one of a nonporous film material or a porous film material.

7. A cover for an ultrasound scanning assembly, wherein the cover exerts compressive force on a patient during use, the cover comprising:
   an outer frame; and
   a film material extending across the outer frame,
   wherein the film material comprises:
      a substrate layer having a first surface and a second surface,
      wherein the substrate layer comprises a solid, non-porous polyurethane film material;
      a first hydrophilic coating layer applied to the first surface of the substrate layer; and
      a second hydrophilic coating layer applied to the second surface of the substrate layer,
      wherein each of the first hydrophilic coating layer and the second hydrophilic coating layer have a thickness ranging from 2 to 5 microns,
      wherein the substrate layer is separate and distinct from the first hydrophilic coating layer and the second hydrophilic coating layer, and
      wherein each of the first hydrophilic coating layer and the second hydrophilic coating layer is configured to be activated using only water or saline to provide a requisite acoustic coupling interface between the ultrasound scanning assembly and the patient.

8. The cover of claim 7, wherein the polyurethane film material has a thickness ranging from approximately 0.025 to 1.00 millimeters.

9. The cover of claim 7, wherein each of the first hydrophilic coating layer and the second hydrophilic coating layer comprises one of an ultra-violet (UV) light curable hydrophilic material or a heat curable hydrophilic material.

10. The cover of claim 9, wherein the first hydrophilic coating layer and the second hydrophilic coating layer comprise a polyvinylpyrrolidone/polyurethane (PVP/PU) or poly methacrylate (PM) coating.

* * * * *